United States Patent
Buehlmayer et al.

(10) Patent No.: US 9,315,500 B2
(45) Date of Patent: Apr. 19, 2016

(54) BICYCLIC HETEROARYL CYCLOALKYLDIAMINE DERIVATIVES

(71) Applicants: Peter Buehlmayer, Arlesheim (CH); Alexander Baxter Smith, Niffer (FR); Gebhard Thoma, Lorrach (DE); Maurice Van Eis, St. Louis (FR)

(72) Inventors: Peter Buehlmayer, Arlesheim (CH); Alexander Baxter Smith, Niffer (FR); Gebhard Thoma, Lorrach (DE); Maurice Van Eis, St. Louis (FR)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/421,439

(22) PCT Filed: Aug. 12, 2013

(86) PCT No.: PCT/IB2013/056589
§ 371 (c)(1),
(2) Date: Feb. 12, 2015

(87) PCT Pub. No.: WO2014/027300
PCT Pub. Date: Feb. 20, 2014

(65) Prior Publication Data
US 2015/0218157 A1 Aug. 6, 2015

Related U.S. Application Data

(60) Provisional application No. 61/682,392, filed on Aug. 13, 2012.

(51) Int. Cl.
C07D 471/04 (2006.01)
A61K 31/5025 (2006.01)
A61K 45/06 (2006.01)

(52) U.S. Cl.
CPC .......... C07D 471/04 (2013.01); A61K 31/5025 (2013.01); A61K 45/06 (2013.01)

(58) Field of Classification Search
CPC ... C07D 471/04; A61K 45/06; A61K 31/5025
USPC ....................... 514/266.2; 544/287
See application file for complete search history.

(56) References Cited

FOREIGN PATENT DOCUMENTS

| WO | 2006/112666 A1 | 10/2006 |
|----|----------------|---------|
| WO | 2007/107469 A1 | 9/2007 |
| WO | 2009/097287 A1 | 8/2009 |
| WO | 2011/014515 A1 | 2/2011 |
| WO | 2011/014795 A2 | 2/2011 |
| WO | 2011/053861 A1 | 5/2011 |
| WO | 2012/097479 A1 | 7/2012 |
| WO | 2012/097682 A1 | 7/2012 |

*Primary Examiner* — Paul V Ward
(74) *Attorney, Agent, or Firm* — John B. Alexander

(57) ABSTRACT

The present invention relates to bicyclic heteroaryl cycloalkyldiamine derivatives, to processes for their production, to their use as SYK inhibitors and to pharmaceutical compositions comprising them. Formula (I)

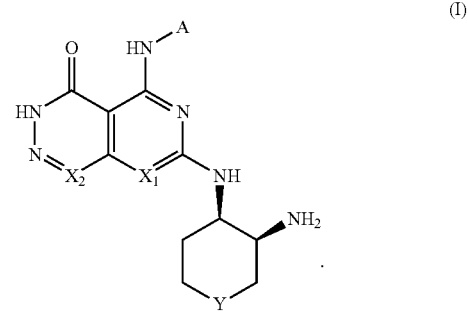

9 Claims, No Drawings

BICYCLIC HETEROARYL CYCLOALKYLDIAMINE DERIVATIVES

This application is a U.S. National Phase filing of International Application No. PCT/IB2013/056589 filed Aug. 12, 2013, which claims priority to U.S. Application No. 61/682,391 filed Aug. 13, 2012, the contents of which are incorporated herein by reference in their entirety.

The present invention relates to bicyclic heteroaryl cycloalkyldiamine derivatives, to processes for their production, to their use as pharmaceuticals and to pharmaceutical compositions comprising them.

Spleen tyrosine kinase (SYK), along with ZAP70, has been described to be a member of the SYK-family of tyrosine kinases. These non-receptor cytoplasmic tyrosine kinases shall share a characteristic dual SH2 domain separated by a linker domain.

It has been further described that SYK may play a central role in the transmission of activating signals within B-cells. Consequently the inhibition of SYK appears to be beneficial in the treatment of autoimmune diseases.

The role of SYK in epithelial malignancies is at present controversial. Several authors have suggested that abnormal SYK function facilitates transformation in nasopharyngeal carcinoma and head and neck cancer while other authors have suggested a tumor suppressor role in breast and gastric cancer.

The compounds of the present invention typically show potent SYK-inhibition, and are therefore potentially useful in the treatment of a wide range of disorders, for example in the treatment of disease and/or disorders associated with the autoimmune system.

The invention therefore provides a compound of the formula (I) or a pharmaceutically acceptable salt thereof,

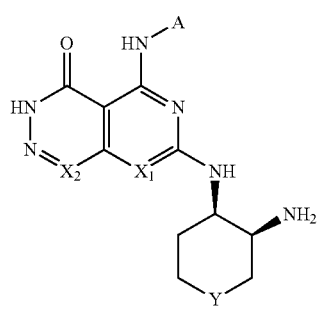

(I)

wherein
X1 is CR1;
X2 is CH;
Y is $CH_2$ or O;
A is bicyclic heteroaryl having from 8 to 10 ring atoms, wherein 1-3 of said ring atoms are heteroatoms selected from N, O and S and wherein said heteroaryl may be unsubstituted of substituted at a carbon atom by a R2 or at a nitrogen atom by a R3;
R1 is H, Hal or $C_{1-4}$ alkyl;
R2 is H, $C_{1-4}$ alkyl, $C_{3-5}$ cycloalkyl, CN or Hal; and
R3 is H or alkyl.

In another embodiment the invention provides a compound of formula (I) or a pharmaceutically acceptable salt thereof, wherein
X1 is CH;
X2 is CH;
Y is $CH_2$;
A is bicyclic heteroaryl having from 8 to 10 ring atoms, wherein 1-2 of said ring atoms are heteroatoms selected from N, O and S and wherein said heteroaryl may be unsubstituted of substituted at a carbon atom by a R2 and at a nitrogen atom by a R3;
R2 is H, $C_{1-4}$ alkyl, $C_{3-5}$ cycloalkyl, CN or Hal; and
R3 is H or alkyl.

In another embodiment the invention provides a compound of formula (I) or a pharmaceutically acceptable salt thereof, wherein
X1 is CH;
X2 is CH;
Y is $CH_2$;
A is bicyclic heteroaryl having from 8 to 10 ring atoms, wherein 1-2 of said ring atoms are N, and said heteroaryl may be unsubstituted of substituted at a carbon atom by a R2; wherein
R2 is H, $C_{1-4}$ alkyl, $C_{3-5}$ cycloalkyl, CN or Hal.

In another embodiment the invention provides a compound of formula (I) or a pharmaceutically acceptable salt thereof, wherein
X1 is CH;
X2 is CH;
Y is $CH_2$;
A is an unsubstituted of substituted indole moiety, wherein the substituent is R2 and is attached to a carbon atom of the indole moiety; wherein
R2 is $C_{1-4}$ alkyl.

In another embodiment the invention provides a compound of formula (I) or a pharmaceutically acceptable salt thereof, wherein
X1 is CH;
X2 is CH;
Y is $CH_2$;
A is an unsubstituted of substituted 7-indolyl moiety, wherein the substituent is R2 and is attached to a carbon atom of the indole moiety; wherein
R2 is $C_{1-4}$ alkyl.

In another embodiment the invention provides a compound of formula (II) or a pharmaceutically acceptable salt thereof, wherein

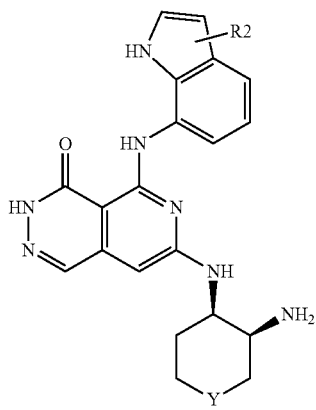

(II)

Y is $CH_2$ or O; and
R2 is H, $C_{1-4}$alkyl or Hal.

In another embodiment the invention provides a compound of formula (II) or a pharmaceutically acceptable salt thereof, wherein Y is CH$_2$; and R2 is H, or C$_{1-4}$alkyl or Hal.

In another embodiment the invention provides a compound of formula (II) or a pharmaceutically acceptable salt thereof, wherein Y is CH$_2$; and R2 is H, methyl or fluoro.

In another embodiment the invention provides a compound of formula (I) or of formula (II) or a pharmaceutically acceptable salt thereof, wherein said compound is selected from:

7-((1R,2S)-2-Amino-cyclohexylamino)-8-fluoro-5-(5-fluoro-3-methyl-1H-indol-7-ylamino)-3H-pyrido[3,4-d]pyridazin-4-one, 7-((1R,2S)-2-Amino-cyclohexylamino)-8-fluoro-5-(quinolin-5-ylamino)-3H-pyrido[3,4-d]pyridazin-4-one, 7-((1R,2S)-2-Amino-cyclohexylamino)-5-(3-methyl-1H-indol-7-ylamino)-3H-pyrido[3,4-d]pyridazin-4-one, 7-((1R,2S)-2-Amino-cyclohexylamino)-5-(1-methyl-1H-indol-4-ylamino)-3H-pyrido[3,4-d]pyridazin-4-one, 7-((1R,2S)-2-Amino-cyclohexylamino)-5-(2-methyl-2H-indazol-4-ylamino)-3H-pyrido[3,4-d]pyridazin-4-one, 7-((1R,2S)-2-Amino-cyclohexylamino)-5-(5-fluoro-3-methyl-1H-indol-7-ylamino)-3H-pyrido[3,4-d]pyridazin-4-one, 7-((1R,2S)-2-Amino-cyclohexylamino)-5-(quinolin-6-ylamino)-3H-pyrido[3,4-d]pyridazin-4-one, 7-((1R,2S)-2-Amino-cyclohexylamino)-5-(benzofuran-4-ylamino)-3H-pyrido[3,4-d]pyridazin-4-one, 7-((1R,2S)-2-Amino-cyclohexylamino)-5-(benzo[b]thiophen-4-ylamino)-3H-pyrido[3,4-d]pyridazin-4-one, 7-((1R,2S)-2-Amino-cyclohexylamino)-5-(2-methyl-quinolin-5-ylamino)-3H-pyrido[3,4-d]pyridazin-4-one, 7-((1R,2S)-2-Amino-cyclohexylamino)-5-(1H-indol-4-ylamino)-3H-pyrido[3,4-d]pyridazin-4-one, 7-((1R,2S)-2-Amino-cyclohexylamino)-5-(1H-indazol-4-ylamino)-3H-pyrido[3,4-d]pyridazin-4-one, 7-((1R,2S)-2-Amino-cyclohexylamino)-5-(quinolin-3-ylamino)-3H-pyrido[3,4-d]pyridazin-4-one, 7-((1R,2S)-2-Amino-cyclohexylamino)-5-(1H-indol-7-ylamino)-3H-pyrido[3,4-d]pyridazin-4-one, 7-((1R,2S)-2-Amino-cyclohexylamino)-5-(8-methyl-quinolin-5-ylamino)-3H-pyrido[3,4-d]pyridazin-4-one, 7-[7-((1R,2S)-2-Amino-cyclohexylamino)-4-oxo-3,4-dihydro-pyrido[3,4-d]pyridazin-5-ylamino]-1H-indole-3-carbonitrile, 7-((1R,2S)-2-Amino-cyclohexylamino)-5-(7-methyl-1H-indol-4-ylamino)-3H-pyrido[3,4-d]pyridazin-4-one, 7-((1R,2S)-2-Amino-cyclohexylamino)-5-(quinolin-5-ylamino)-3H-pyrido[3,4-d]pyridazin-4-one, 7-((1R,2S)-2-Amino-cyclohexylamino)-5-(2-methyl-1H-indol-4-ylamino)-3H-pyrido[3,4-d]pyridazin-4-one, 7-((1R,2S)-2-Amino-cyclohexylamino)-5-(quinoxalin-6-ylamino)-3H-pyrido[3,4-d]pyridazin-4-one, 7-((1R,2S)-2-Amino-cyclohexylamino)-5-(quinolin-7-ylamino)-3H-pyrido[3,4-d]pyridazin-4-one, 7-((1R,2S)-2-Amino-cyclohexylamino)-5-(quinolin-8-ylamino)-3H-pyrido[3,4-d]pyridazin-4-one, 7-((3R,4R)-3-Amino-tetrahydro-pyran-4-ylamino)-5-(3-methyl-1H-indol-7-ylamino)-3H-pyrido[3,4-d]pyridazin-4-one, 7-((3R,4R)-3-Amino-tetrahydro-pyran-4-ylamino)-5-(benzo[b]thiophen-4-ylamino)-3H-pyrido[3,4-d]pyridazin-4-one, 7-((3R,4R)-3-Amino-tetrahydro-pyran-4-ylamino)-5-(5-fluoro-3-methyl-1H-indol-7-ylamino)-3H-pyrido[3,4-d]pyridazin-4-one, and 7-((3R,4R)-3-Amino-tetrahydro-pyran-4-ylamino)-5-(1H-indol-7-ylamino)-3H-pyrido[3,4-d]pyridazin-4-one.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "halogen" or "halo" refers to fluoro, chloro, bromo, and iodo.

As used herein, the term "cycloalkyl" refers to saturated or unsaturated monocyclic, bicyclic, tricyclic or spirocyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms.

A substituted cycloalkyl is a cycloylkyl group substituted by one, or two, or three, or more substituents independently selected from the group consisting of hydroxyl, thiol, cyano, nitro, oxo, alkylimino, C$_1$-C$_4$-alkenyl, C$_1$-C$_4$-alkynyl, C$_1$-C$_4$-alkoxy, C$_1$-C$_4$-thioalkyl, C$_1$-C$_4$-alkenyloxy, C$_1$-C$_4$-alkynyloxy, halogen, C$_1$-C$_4$-alkylcarbonyl, carboxy, C$_1$-C$_4$-alkoxycarbonyl, amino, C$_1$-C$_4$-alkylamino, di-C$_1$-C$_4$-alkylamino, C$_1$-C$_4$-alkylaminocarbonyl, di-C$_1$-C$_4$-alkylaminocarbonyl, C$_1$-C$_4$-alkylcarbonylamino, C$_1$-C$_4$-alkylcarbonyl(C$_1$-C$_4$-alkyl)amino, sulfonyl, sulfamoyl, alkylsulfamoyl, C$_1$-C$_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or C$_1$-C$_4$-alkoxy groups. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Unless defined differently, the term "heteroaryl" refers to a 5-14 membered monocyclic- or bicyclic- or tricyclic-aromatic ring system, having 1 to 8 heteroatoms. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms.

Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) and/or (II) that contain groups capable of acting as donors and/or acceptors for hydrogen bonds may be capable of forming co-crystals with suitable co-crystal formers. These co-crystals may be prepared from compounds of the invention by known co-crystal forming procedures. Such procedures include grinding, heating, co-subliming, co-melting, or contacting in solution compounds of the invention with the co-crystal former under crystallization conditions and isolating co-crystals thereby formed. Suitable co-crystal formers include those described in WO 2004/078163. Hence the invention further provides co-crystals comprising a compound of the invention.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by SYK, or (ii) associated with SYK activity, or (iii) characterized by activity (normal or abnormal) of SYK; or (2) reducing or inhibiting the activity of SYK; or (3) reducing or inhibiting the expression of SYK. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of SYK; or at least partially reducing or inhibiting the expression of SYK.

The term "subject" as used herein may refer to an animal. The animal may be a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of the invention may be prepared according to the Schemes provided infra:

Methods of Synthesizing

Agents of the invention, i.e. compounds in accordance to the definition of formula (I) or (II) may be prepared by a reaction sequence explicitly shown in the reaction schemes 1-3 of the experimental part (see hereinbelow).

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc. Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

EXPERIMENTAL SECTION

1. Analytical Methods as Used in the Examples

Liquid chromatography as used in the examples:
UPLC/MS: Waters Acquity UPLC+Waters ZQ2000 MS
UV-PDA: 210-450 nM
MS range: 100-1200 Da
Column: Acquity HSS T3 2.1×50 mm 1.8µ at 60° C.
Mobile phase: A: water+0.05% formic acid
B: acetonitrile+0.04% formic acid

| Time [minutes] | Flow [ml/min] | A [%] | B [%] |
| --- | --- | --- | --- |
| 0.00 | 1.000 | 95 | 5 |
| 1.40 | 1.000 | 2 | 98 |
| 1.80 | 1.000 | 2 | 98 |
| 1.90 | 1.000 | 95 | 5 |
| 2.00 | 1.000 | 95 | 5 |

2. Preparative HPLC as Used in the Examples

Column: Waters SunFire 30×100 mm, C18, 5 µm
Flow: 20 ml/min
Solvent: Acetonitril/water/0.1% TFA (gradient)

3. Flash Chromatography as Used in the Examples

Column: Redisept 12 g silicagel column
Solvent: EtOAc/MeOH (+0.1% NH3) 1:0 (2 min)=>0:1 (15 min) gradient

ABBREVIATIONS

DCM: Dichloromethane
DIPEA: N,N-Diisopropylethylamine
DMF: Dimethylformamide
DMSO: Dimethylsulfoxide
EtOAc: Ethyl actetate
HPLC: High Pressure Liquid Chromatography
i-PrOH: Isopropanol
MeOH: Methanol
NMP: N-Methyl-2-pyrrolidon
RT: Room temperature
TFA: Trifluoroacetic acid
THF: Tetrahydrofuran
UPLC: Ultra Performance Liquid Chromatography To the extent compounds are mentioned as such in a reaction scheme and/or within the full experimental part, such a compound is either commerically available or if not, has been fully described in the prior art, and hence can be obtained accordingly for carrying out a corresponding reaction step.

Example 1.1

7-((1R,2S)-2-Amino-cyclohexylamino)-8-fluoro-5-(5-fluoro-3-methyl-1H-indol-7-ylamino)-3H-pyrido[3,4-d]pyridazin-4-one Example 1.1 was synthesized in accordance to Scheme 1 shown below:

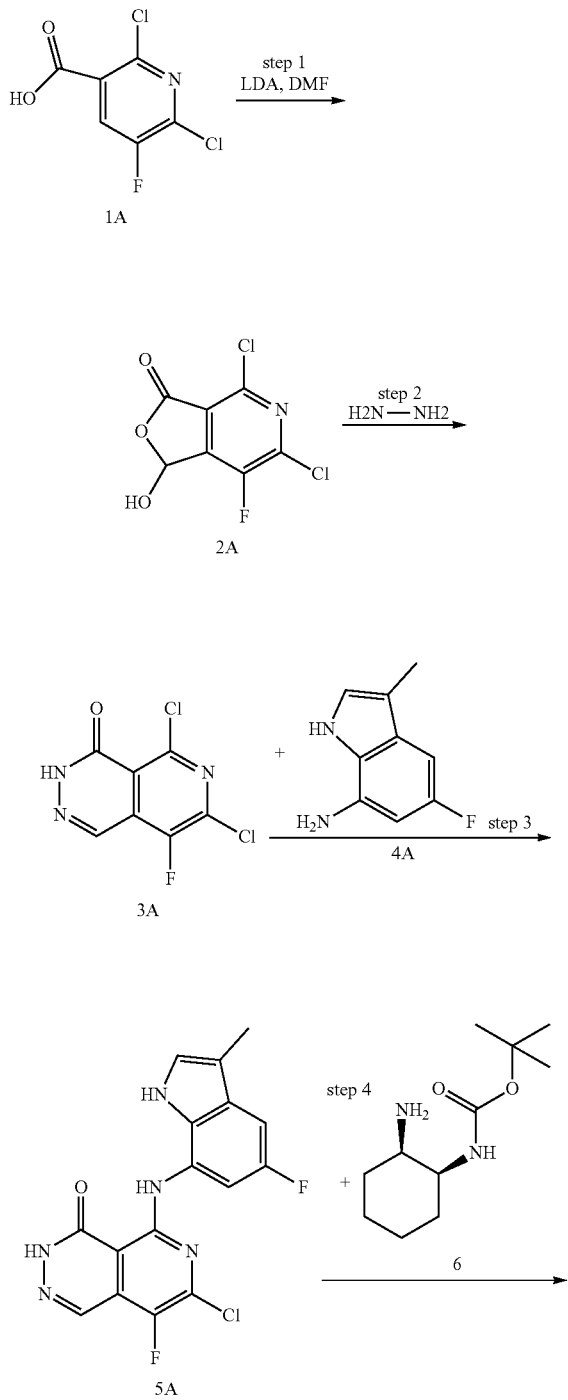

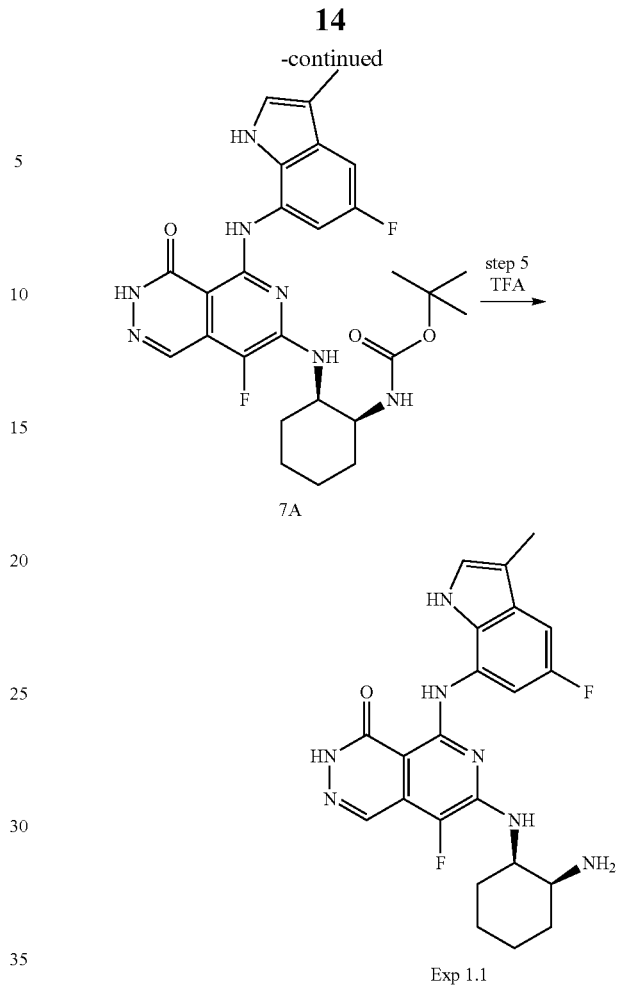

Step 1: A 1.6 M solution of n-BuLi in hexane (31.3 ml, 50 mmol) was added to THF (45 ml) under nitrogen at −78° C., followed by dropwise addition of diisopropylamine (5.06 g, 50 mmol) during 15 min. The resulting solution was stirred for 75 min. at −78° C. Then a solution of 1A (3.0 g, 14.3 mmol) in THF (6 ml) was added dropwise during 10 min. The resulting reaction mixture was stirred for 1 h at −78° C. before dropwise addition of DMF (10.0 ml, 129 mmol). The reaction mixture was stirred for 30 min. at −78° C., 30 min. at −50° C. and finally warmed up to RT. Water was added to the reaction mixture, followed by the addition of a 1 M aqueous HCl solution until the pH was below 7. The solution was extracted with EtOAc and the combined organic layers were washed with brine, dried over $Na_2SO_4$, filtered and concentrated at reduced pressure to give crude 2A as a yellow oil (4.2 g, containing some remaining DMF). The crude material was used in the next step without further purification. UPLC/MS found for C7H2Cl2NO3 as (M−H)⁻ 236.0; UPLC retention time 0.75 min.

Step 2: To a solution of crude 2A (4.2 g) in water (85 ml) was added hydrazine sulfate (4.65 g, 35.7 mmol) and sodium acetate trihydrate (5.83 g, 42.9 mmol). The resulting reaction mixture was heated to reflux for 1 h until reaction monitoring by UPLC-MS indicated complete conversion of the starting material. The reaction mixture was cooled to RT, diluted with water and extracted with EtOAc. The combined organic layers were washed with a saturated aqueous sodium bicarbonate solution, dried over $Na_2SO_4$, filtered and concentrated at reduced pressure to afford 3A as a yellow solid. UPLC/MS found for C7H2Cl2FN3O as (M−H)⁻ 232.0; UPLC retention time 0.73 min.

Step 3: In a microwave vial, 4A (232 mg, 1.41 mmol) and DIPEA (249 mg, 1.93 mmol) were added to a solution of 3A (1.29 mmol, 301 mg) in i-PrOH (3 ml). The vial was capped and the reaction mixture was heated under nitrogen for 15 h at 110° C. After cooling down to RT, the reaction mixture was poured into water and extracted with EtOAc. The combined organic layers were washed with brine, dried over Na$_2$SO$_4$, filtered and concentrated at reduced pressure. The residue was triturated with DCM, filtered and dried under vacuum to afford pure 5A as a brown powder. UPLC/MS found for C16H10ClF2N5O as (M−H)$^-$ 360.0; UPLC retention time 1.17 min.

Step 4: In a microwave vial, 6 (49 mg, 0.23 mmol) and DIPEA (30 mg, 0.23 mmol) were added to a solution of 5A (55 mg, 0.15 mmol) in NMP (5 ml). The vial was capped and the reaction mixture was heated under nitrogen for 18 h at 110° C. After cooling down to RT, the reaction mixture was poured into water and extracted with EtOAc. The combined organic layers were washed with brine, dried over Na$_2$SO$_4$, filtered and concentrated at reduced pressure to afford crude 7A as black oil. The crude product was used in the next step without further purification. UPLC/MS found for C27H31F2N7O3 as (M+H)$^+$ 540.1; UPLC retention time 1.33 min.

Step 5: To a solution of crude 7A (82 mg, 0.15 mmol) in DCM (10 ml), TFA (2 ml) was added and the resulting solution was stirred for 5 h at RT. The reaction mixture was concentrated at reduced pressure and the crude product was dissolved in MeOH, filtered through a micropore filter and purified by preparative HPLC to afford Example 1.1 as a yellow solid. $^1$H-NMR (400 MHz; DMSO-d6, 25° C.): 12.68 (s, 1H); 10.94 (s, 1H); 10.56 (s, 1H); 8.23 (s, 1H); 7.95-7.85 (bs, 2H); 7.43-7.37 (d, 1H); 7.32-7.26 (m, 1H); 7.14 (s, 1H); 7.08-7.02 (d, 2H); 3.92-3.82 (m, 1H); 3.45-3.35 (m, 1H); 2.23 (s, 3H); 1.84-1.46 (m, 4H); 1.42-1.14 (m, 4H); UPLC/MS found for C22H23F2N7O as (M+H)$^+$ 440.1; UPLC retention time 0.77 min.

Example 1.2 was prepared following procedures similar to those described for Example 1.1. The only difference in the above reaction scheme was the use of 5-aminoquinoline instead of compound 4A as the reaction partner in reaction step 3.

7-((1R,2S)-2-Amino-cyclohexylamino)-8-fluoro-5-(quinolin-5-ylamino)-3H-pyrido[3,4-d]pyridazin-4-one

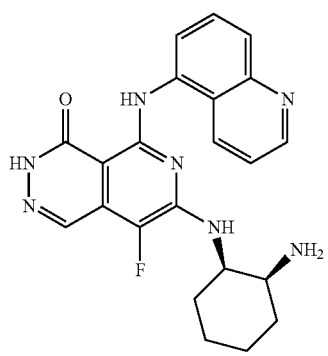 [SMILES: N[C@H]1CCCC[C@H]1Nc1nc(Nc2cccc3ncccc23)c2c(=O)[nH]ncc2c1F]

The compound was characterised after purification by preparative HPLC.

$^1$H-NMR (400 MHz; DMSO-d6, 25° C.): 12.72 (s, 1H); 11.91 (s, 1H); 9.02-8.97 (dd, 1H); 8.60-8.54 (dd, 1H); 8.39-8.45 (dd, 1H); 8.29 (s, 1H); 7.85-7.79 (m, 2H); 7.75-7.65 (m, 3H); 7.32-7.26 (d, 1H); 4.12-4.06 (m, 1H); 3.58-3.52 (m, 1H); 1.85-1.75 (m, 2H); 1.72-1.62 (m, 2H); 1.58-1.32 (m, 4H); UPLC/MS found for C22H22FN7O as (M+H)$^+$ 420.1; UPLC retention time 0.54 min.

Preparation of 3-methyl-5-fluoro-7-amino-indole

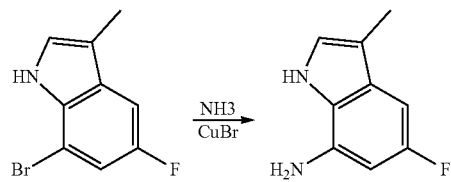

A mixture of 7-bromo-5-fluoro-3-methyl-indole (2.5 g), Cu (0.77 g), CuBr (1.57 g) and NH$_3$ (30 ml of a 33% aqueous solution) was heated in an autoclave for 2 h at 170° C. The mixture was diluted with water and extracted with EtOAc. The organic phase was dried and the solvent removed to give 3-methyl-5-fluoro-7-amino-indole as an oil which was used without further purification. UPLC/MS found for C9H9FN2 as (M+H)$^+$165.2

Preparation of 5-fluoro-7-amino-indole

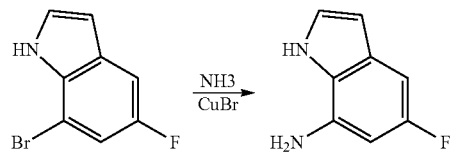

A mixture of 7-bromo-5-fluoro-indole (1 g), Cu (0.31 g), CuBr (0.64 g) and NH$_3$ (30 ml of a 33% aqueous solution) was heated in an autoclave for 1.5 h at 155° C. The mixture was diluted with water and extracted with EtOAc. The organic phase was dried and the solvent removed to give 5-fluoro-7-amino-indole as an oil which was used without further purification. UPLC/MS found for C8H7FN2 as (M+H)$^+$ 151.0.

Example 2.1

7-((1R,2S)-2-Amino-cyclohexylamino)-5-(3-methyl-1H-indol-7-ylamino)-3H-pyrido[3,4-d]pyridazin-4-one Example 2.1 was synthesized in accordance to Scheme 2 depicted below:

Scheme 2

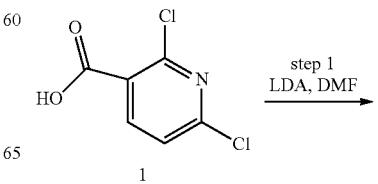

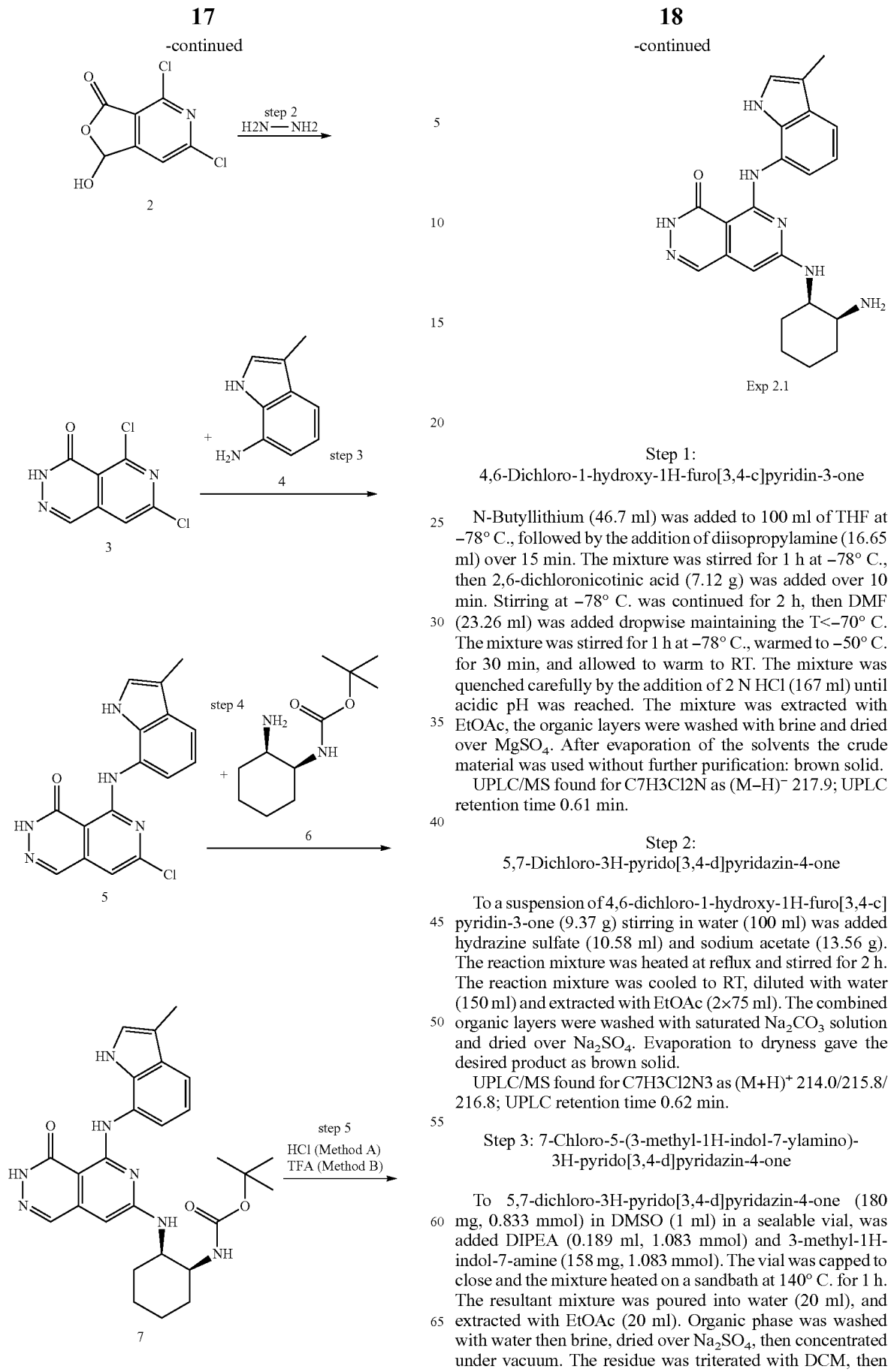

Step 1:
4,6-Dichloro-1-hydroxy-1H-furo[3,4-c]pyridin-3-one

N-Butyllithium (46.7 ml) was added to 100 ml of THF at −78° C., followed by the addition of diisopropylamine (16.65 ml) over 15 min. The mixture was stirred for 1 h at −78° C., then 2,6-dichloronicotinic acid (7.12 g) was added over 10 min. Stirring at −78° C. was continued for 2 h, then DMF (23.26 ml) was added dropwise maintaining the T<−70° C. The mixture was stirred for 1 h at −78° C., warmed to −50° C. for 30 min, and allowed to warm to RT. The mixture was quenched carefully by the addition of 2 N HCl (167 ml) until acidic pH was reached. The mixture was extracted with EtOAc, the organic layers were washed with brine and dried over $MgSO_4$. After evaporation of the solvents the crude material was used without further purification: brown solid.

UPLC/MS found for C7H3Cl2N as (M−H)− 217.9; UPLC retention time 0.61 min.

Step 2:
5,7-Dichloro-3H-pyrido[3,4-d]pyridazin-4-one

To a suspension of 4,6-dichloro-1-hydroxy-1H-furo[3,4-c]pyridin-3-one (9.37 g) stirring in water (100 ml) was added hydrazine sulfate (10.58 ml) and sodium acetate (13.56 g). The reaction mixture was heated at reflux and stirred for 2 h. The reaction mixture was cooled to RT, diluted with water (150 ml) and extracted with EtOAc (2×75 ml). The combined organic layers were washed with saturated $Na_2CO_3$ solution and dried over $Na_2SO_4$. Evaporation to dryness gave the desired product as brown solid.

UPLC/MS found for C7H3Cl2N3 as (M+H)+ 214.0/215.8/216.8; UPLC retention time 0.62 min.

Step 3: 7-Chloro-5-(3-methyl-1H-indol-7-ylamino)-3H-pyrido[3,4-d]pyridazin-4-one To 5,7-dichloro-3H-pyrido[3,4-d]pyridazin-4-one (180 mg, 0.833 mmol) in DMSO (1 ml) in a sealable vial, was added DIPEA (0.189 ml, 1.083 mmol) and 3-methyl-1H-indol-7-amine (158 mg, 1.083 mmol). The vial was capped to close and the mixture heated on a sandbath at 140° C. for 1 h. The resultant mixture was poured into water (20 ml), and extracted with EtOAc (20 ml). Organic phase was washed with water then brine, dried over $Na_2SO_4$, then concentrated under vacuum. The residue was triterated with DCM, then collected by filtration and dried to give title compound as a yellow-mustard coloured solid.

UPLC/MS found for C16H12ClN5O as (M+H)+ 326.1; UPLC retention time 1.10 min.

Step 4: {(1S,2R)-2-[5-(3-Methyl-1H-indol-7-ylamino)-4-oxo-3,4-dihydro-pyrido[3,4-d]pyridazin-7-ylamino]-cyclohexyl}-carbamic acid tert-butyl ester To 7-chloro-5-(3-methyl-1H-indol-7-ylamino)-3H-pyrido[3,4-d]pyridazin-4-one (177 mg, 0.543 mmol) in NMP (1 ml) in a sealable glass vial, was added DIPEA (0.190 ml, 1.087 mmol) and tert-butyl(1S,2R)-2-aminocyclohexylcarbamate (233 mg, 1.087 mmol). The vial was capped to close and the reaction mixture was heated on a sandbath at 120° C. for 3 days. The resulting mixture was poured into water (20 ml), and extracted with EtOAc (20 ml). The organic phase was washed with water and brine, dried over $Na_2SO_4$, then concentrated under vacuum. The residue was triterated with DCM, then collected by filtration and dried to give a gummy solid.

Step 5 (Method A):

The crude gum was dissolved in DCM (4 ml)/MeOH (0.5 ml) and to this was added 4 N HCl in dioxan (1.358 ml, 5.43 mmol). The reaction mixture was stirred for 4 h at RT before concentrating under vacuum. The resultant residue was triterated with diethyl ether. The solvent was removed by decanting and the residue was dried on a rotavap. The resultant crude solid residue was dissolved in 2 ml NMP, filtered through a micropore filter and purified by preparative HPLC. Fractions containing product were combined and applied to a scx-2 cartridge, releasing free base by eluting with a 1 N $NH_3$-solution in MeOH. The solvent was removed to afford the title compound as a yellow solid.

$^1$H-NMR (400 MHz; DMSO-d6, 25° C.): 12.11 (br.s, 1H); 11.10 (s, 1H); 10.39 (s, 1H); 7.90 (s, 1H), 7.44-7.49 (m, 1H); 7.24-7.29 (d, 1H); 7.05 (br.s, 1H); 6.93-7.00 (t, 1H); 6.85-7.10 (br.s, 1H); 3.65-3.79 (m, 1H); 2.88-2.95 (m, 1H); 2.28 (s, 3H); 0.71-1.79 (m, 8H); UPLC/MS found for C21H22N6O2 as (M+H)+ 404.2; UPLC retention time 0.76 min.

Step 5 (Method B): 7-((1R,2S)-2-Amino-cyclohexylamino)-5-(3-methyl-1H-indol-7-ylamino)-3H-pyrido[3,4-d]pyridazin-4-one In a 20 ml round-bottomed flask {(1S,2R)-2-[5-(3-methyl-1H-indol-7-ylamino)-4-oxo-3,4-dihydro-pyrido[3,4-d]pyridazin-7-ylamino]-cyclohexyl}-carbamic acid tert-butyl ester (76 mg, 0.150 mmol) was dissolved in DCM (1 ml) and TFA (0.347 ml, 4.51 mmol) was added to give a yellow solution. The mixture was stirred at RT until reaction was completed (1 h). The reaction mixture was diluted with 30 ml of EtOAc and washed with 20 ml of 5% $Na_2CO_3$ solution, followed by 2×30 ml of water. Aqueous phases were re-extracted with 30 ml of EtOAc. The combined organic phases were dried and evaporated to yield a yellow solid. The crude product was purified by flash-chromatography and finally freeze dried from tert.BuOH. $^1$H-NMR, UPLC/MS and UPLC retention time as described.

Examples 2.2-2.20 were prepared following procedures similar to those described for Example 2.1. The only deviating reaction partner in the above reaction scheme 2 were the appropriate substituted aniline-compounds listed in the above scheme as compound 4.

Example 2.2 was prepared following procedures similar to those described for Example 2.1. The BOC-deprotection was done by Method A as described for Example 2.1 step 5. The only difference in the above reaction scheme was the use of 1-methyl-1H-indol-4-ylamine instead of compound 4 as the reaction partner reaction step 3.

7-((1R,2S)-2-Amino-cyclohexylamino)-5-(1-methyl-1H-indol-4-ylamino)-3H-pyrido[3,4-d]pyridazin-4-one

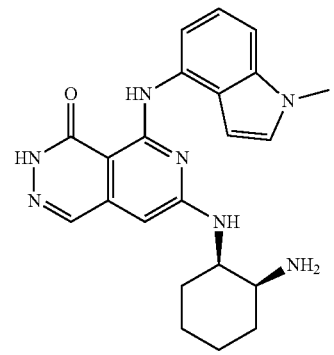 [SMILES: Cn1ccc2c(Nc3nc(N[C@@H]4CCCC[C@@H]4N)cc4cn[nH]c(=O)c34)cccc21]

The compound was characterised after purification by preparative HPLC.

$^1$H-NMR (400 MHz; DMSO-d6, 25° C.): 12.162 (br.s, 1H); 11.90 (s, 1H); 8.30-8.36 (m, 1H); 7.92 (s, 1H); 7.33-7.36 (d, 1H); 7.09-7.23 (m, 3H); 6.57-6.59 (d, 1H); 6.05 (s, 1H); 3.92-4.15 (m, 1H); 3.81 (s, 3H); 3.18-3.23 (m, 1H); 1.32-1.81 (m, 8H); UPLC/MS found for C22H25N7O as (M+H)+ 404.3; UPLC retention time 0.75 min.

Example 2.3 was prepared following procedures similar to those described for Example 2.1. The BOC-deprotection was done by Method B as described for Example 2.1 step 5. The only difference in the above reaction scheme was the use of 2-methyl-2H-indazol-4-ylamine instead of compound 4 as the reaction partner reaction step 3.

7-((1R,2S)-2-Amino-cyclohexylamino)-5-(2-methyl-2H-indazol-4-ylamino)-3H-pyrido[3,4-d]pyridazin-4-one

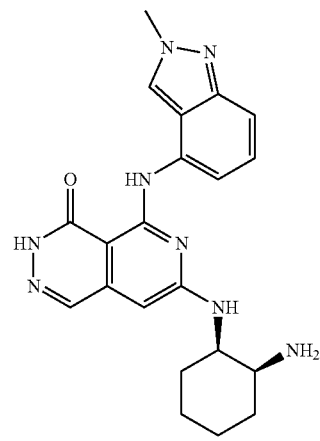 [SMILES: Cn1cc2c(Nc3nc(N[C@@H]4CCCC[C@@H]4N)cc4cn[nH]c(=O)c34)cccc2n1]

The compound was characterised after purification by preparative HPLC.

¹H-NMR (400 MHz; DMSO-d6, 25° C.): 12.38 (s, 1H); 11.97 (s, 1H); 8.33 (s, 1H); 7.98-8.08 (m, 1H); 7.80 (br.s, 2H); 7.38 (br.s, 1H); 7.29-7.20 (m, 2H); 6.18 (s, 1H); 4.31 (br.s, 1H); 4.22 (s, 3H); 3.69 (br.s, 1H); 1.84-1.47 (m, 8H); UPLC/MS found for C21H24N8O as (M+H)⁺ 405.1; UPLC retention time 0.64 min.

Example 2.4 was prepared following procedures similar to those described for Example 2.1. The BOC-deprotection was done by Method B as described for Example 2.1 step 5. The only difference in the above reaction scheme was the use of 5-fluoro-3-methyl-1H-indol-7-ylamine instead of compound 4 as the reaction partner reaction step 3.

7-((1R,2S)-2-Amino-cyclohexylamino)-5-(5-fluoro-3-methyl-1H-indol-7-ylamino)-3H-pyrido[3,4-d]pyridazin-4-one

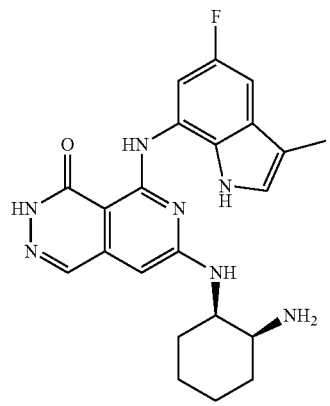 [SMILES: Cc1c[nH]c2c(Nc3nc(N[C@@H]4CCCC[C@@H]4N)cc4cn[nH]c(=O)c34)cc(F)cc12]

The compound was characterised after purification by preparative HPLC.

¹H-NMR (400 MHz, DMSO-d₆) 12.32 (s, 1H); 11.22 (s, 1H); 10.56 (s, 1H); 8.03 (s, 1H); 7.65 (br.s, 2H); 7.51 (d, 1H); 7.25 (br.s, 1H); 7.14 (s, 1H); 7.03 (dd, 1H); 6.12 (s, 1H); 3.97 (br.s, 2H); 3.42 (br.s, 1H); 2.2 (s, 3H); 1.74-1.33 (m, 8H); UPLC/MS found for C22H24FN7O as (M+H)⁺ 422.3; UPLC retention time 0.75 min.

Example 2.5 was prepared following procedures similar to those described for Example 2.1. The BOC-deprotection was done by Method B as described for Example 2.1 step 5. The only difference in the above reaction scheme was the use of quinolin-6-ylamine instead of compound 4 as the reaction partner reaction step 3.

7-((1R,2S)-2-Amino-cyclohexylamino)-5-(quinolin-6-ylamino)-3H-pyrido[3,4-d]pyridazin-4-one

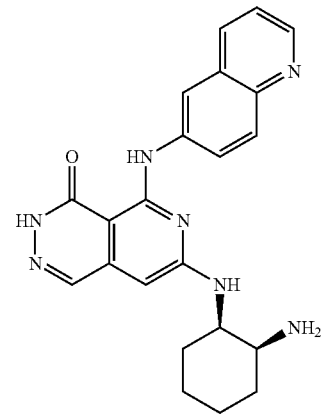 [SMILES: N[C@H]1CCCC[C@H]1Nc1cc2cn[nH]c(=O)c2c(Nc2ccc3ncccc3c2)n1]

The compound was characterised after purification by preparative HPLC.

¹H-NMR (400 MHz; DMSO-d6, 25° C.): 12.3 (br.s, 1H); 11.9 (s, 1H); 8.76 (dd, 1H); 8.56 (br.s, 1H); 8.25 (d, 1H); 8.03-7.91 (m, 3H); 7.52 (dd, 1H); 7.30 (br.s, 1H); 6.18 (s, 1H); 4.30 (br.s, 1H); 3.40 (br.s, 1H); 1.95-1.20 (m, 8H); UPLC/MS found for C22H23N7O as (M+H)⁺402.3; UPLC retention time 0.62 min.

Example 2.6 was prepared following procedures similar to those described for Example 2.1. The BOC-deprotection was done by Method A as described for Example 2.1 step 5. The only difference in the above reaction scheme was the use of benzofuran-4-ylamine instead of compound 4 as the reaction partner reaction step 3.

7-((1R,2S)-2-Amino-cyclohexylamino)-5-(benzofuran-4-ylamino)-3H-pyrido[3,4-d]pyridazin-4-one

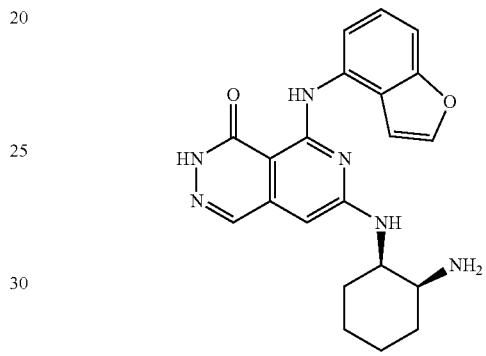

The compound was characterised after purification by preparative HPLC.

¹H-NMR (400 MHz; DMSO-d6, 25° C.): 12.23 (br.s, 1H); 11.98 (s, 1H); 8.40-8.48 (m, 1H); 8.02-8.03 (d, 1H); 7.96 (s, 1H); 7.18-7.34 (m, 3H); 6.95-6.98 (d, 1H); 6.11 (s, 1H); 3.90-4.09 (m, 1H); 3.14-3.21 (m, 1H); 1.30-1.79 (m, 8H); UPLC/MS found for C21H22N6O2 as (M+H)⁺ 391.2; UPLC retention time 0.76 min.

Example 2.7 was prepared following procedures similar to those described for Example 2.1. The BOC-deprotection was done by Method B as described for Example 2.1 step 5. The only difference in the above reaction scheme was the use of benzo[b]thiophen-4-ylamine instead of compound 4 as the reaction partner reaction step 3.

7-((1R,2S)-2-Amino-cyclohexylamino)-5-(benzo[b]thiophen-4-ylamino)-3H-pyrido[3,4-d]pyridazin-4-one

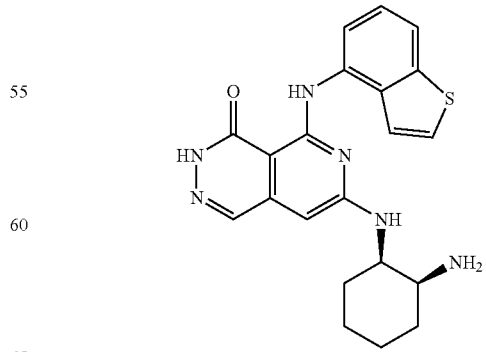

The compound was characterised after purification by preparative HPLC.

¹H-NMR (400 MHz; DMSO-d6, 25° C.): 12.41 (s, 1H); 12.15 (s, 1H); 8.07 (s, 1H); 7.86 (d, 1H); 7.78 (br.s, 2H); 7.71 (d, 1H); 7.62 (d, 1H); 7.40 (dd, 2H); 6.18 (s, 1H); 4.30 (br.s, 1H); 3.65 (br.s, 1H); 1.91-1.46 (m, 8H); UPLC/MS found for C21H22N6OS as (M+H)⁺ 407.3; UPLC retention time 0.79 min.

Example 2.8 was prepared following procedures similar to those described for Example 2.1. The BOC-deprotection was done by Method B as described for Example 2.1 step 5. The only difference in the above reaction scheme was the use of 2-methyl-quinolin-5-ylamine instead of compound 4 as the reaction partner reaction step 3.

7-((1R,2S)-2-Amino-cyclohexylamino)-5-(2-methyl-quinolin-5-ylamino)-3H-pyrido[3,4-d]pyridazin-4-one

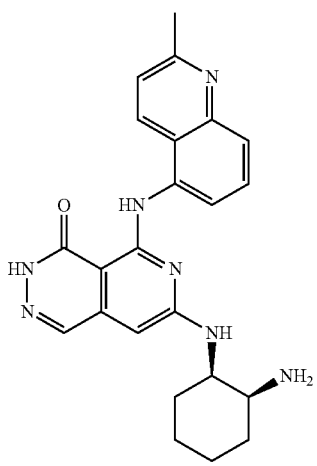 [SMILES: Cc1ccc2c(Nc3nc(N[C@@H]4CCCC[C@@H]4N)cc4cn[nH]c(=O)c34)cccc2n1]

The compound was characterised after purification by preparative HPLC.

¹H-NMR (400 MHz; DMSO-d6, 25° C.): 12.46 (s, 1H); 12.27 (br.s, 1H); 8.75-8.58 (m, 2H); 8.10 (s, 1H); 7.89-7.67 (m, 5H); 7.42 (br.s, 1H); 6.22 (s, 1H); 4.16 (br.s, 1H); 3.54 (br.s, 1H); 2.78 (s, 3H); 1.96-1.35 (m, 8H); UPLC/MS found for C23H25N7O as (M+H)⁺ 416.1; UPLC retention time 0.50 min.

Example 2.9 was prepared following procedures similar to those described for Example 2.1. The BOC-deprotection was done by Method A as described for Example 2.1 step 5. The only difference in the above reaction scheme was the use of 1H-indol-4-ylamine instead of compound 4 as the reaction partner reaction step 3.

7-((1R,2S)-2-Amino-cyclohexylamino)-5-(1H-indol-4-ylamino)-3H-pyrido[3,4-d]pyridazin-4-one

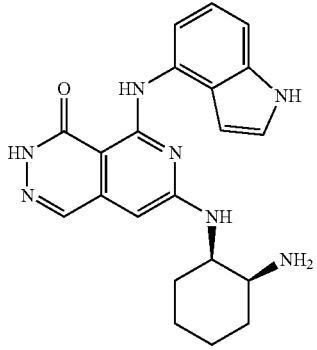 [SMILES: N[C@H]1CCCC[C@H]1Nc1cc2cn[nH]c(=O)c2c(Nc2cccc3[nH]ccc23)n1]

The compound was characterised after purification by preparative HPLC.

¹H-NMR (400 MHz; DMSO-d6, 25° C.): 12.15 (br.s, 1H); 11.89 (s, 1H); 11.18 (s, 1H); 8.25-8.30 (d, 1H); 7.92 (s, 1H); 7.34-7.37 (t, 1H); 7.03-7.22 (m, 3H); 6.58-6.62 (m, 1H); 6.05 (s, 1H); 3.96-4.10 (m, 1H); 3.17-3.22 (m, 1H); 1.31-1.80 (m, 8H); UPLC/MS found for C21H23N7O as (M+H)⁺ 390.2; UPLC retention time 0.67 min.

Example 2.10 was prepared following procedures similar to those described for Example 2.1. The BOC-deprotection was done by Method A as described for Example 2.1 step 5. The only difference in the above reaction scheme was the use of 1H-indazol-4-ylamine instead of compound 4 as the reaction partner reaction step 3.

7-((1R,2S)-2-Amino-cyclohexylamino)-5-(1H-indazol-4-ylamino)-3H-pyrido[3,4-d]pyridazin-4-one

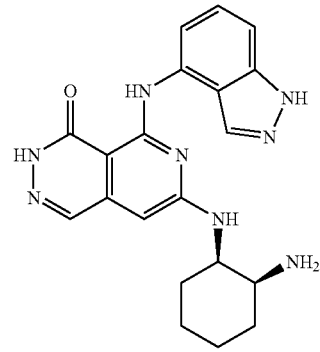 [SMILES: N[C@H]1CCCC[C@H]1Nc1cc2cn[nH]c(=O)c2c(Nc2cccc3[nH]ncc23)n1]

The compound was characterised after purification by preparative HPLC.

¹H-NMR (400 MHz; DMSO-d6, 25° C.): 13.20 (br.s, 1H); 12.20 (s, 1H); 8.22-8.35 (m, 1H); 8.19 (s, 1H); 7.98 (s, 1H); 7.13-7.47 (m, 3H); 6.13 (s, 1H); 3.90-4.19 (m, 1H); 3.15-3.28 (m, 1H); 1.22-1.84 (m, 8H); UPLC/MS found for C20H22N8O as (M+H)⁺ 391.1; UPLC retention time 0.59 min.

Example 2.11 was prepared following procedures similar to those described for Example 2.1. The BOC-deprotection was done by Method B as described for Example 2.1 step 5. The only difference in the above reaction scheme was the use of quinolin-3-ylamine instead of compound 4 as the reaction partner reaction step 3.

7-((1R,2S)-2-Amino-cyclohexylamino)-5-(quinolin-3-ylamino)-3H-pyrido[3,4-d]pyridazin-4-one

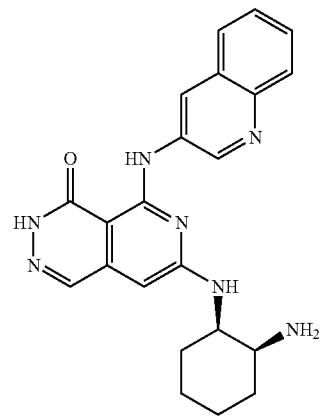 [SMILES: N[C@H]1CCCC[C@H]1Nc1cc2cn[nH]c(=O)c2c(Nc2cnc3ccccc3c2)n1]

The compound was characterised after purification by preparative HPLC.

$^1$H-NMR (400 MHz; DMSO-d6, 25° C.): 12.2 (br.s, 1H); 11.9 (s, 1H); 8.96 (br.s, 2H); 8.02 (s, 2H); 7.88 (br.s, 1H); 7.68-7.58 (m, 2H); 7.30 (br.s, 1H); 6.2 (s, 1H); 4.20 (br.s, 1H); 3.40 (br.s, 1H); 1.90-1.20 (m, 8H); UPLC/MS found for C22H23N7O as (M+H)$^+$ 402.1; UPLC retention time 0.67 min.

Example 2.12 was prepared following procedures similar to those described for Example 2.1. The BOC-deprotection was done by Method A as described for Example 2.1 step 5. The only difference in the above reaction scheme was the use of 1H-indol-7-ylamine instead of compound 4 as the reaction partner reaction step 3.

7-((1R,2S)-2-Amino-cyclohexylamino)-5-(1H-indol-7-ylamino)-3H-pyrido[3,4-d]pyridazin-4-one

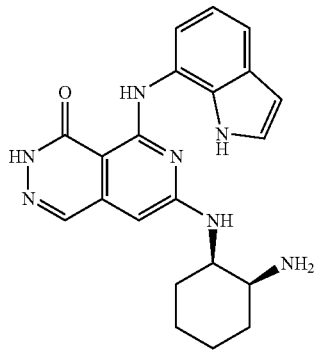 [SMILES: N[C@H]1CCCC[C@H]1Nc1cc2cn[nH]c(=O)c2c(Nc2cccc3cc[nH]c23)n1]

The compound was characterised after purification by preparative HPLC.

$^1$H-NMR (400 MHz; DMSO-d6, 25° C.): 12.09 (br.s, 1H); 11.09 (s, 1H); 10.75 (s, 1H); 7.89 (s, 1H); 7.40-7.44 (d, 1H); 7.33-7.37 (d, 1H); 7.26-7.28 (t, 1H); 6.88-7.05 (br.s, 1H); 6.94-6.99 (t, 1H); 6.45-6.48 (m, 1H), 6.01 (s, 1H); 3.62-3.74 (m, 1H); 2.88-2.92 (m, 1H); 1.05-1.59 (m, 8H); UPLC/MS found for C21H23N7O as (M+H)$^+$ 390.1; UPLC retention time 0.70 min.

Example 2.13 was prepared following procedures similar to those described for Example 2.1. The BOC-deprotection was done by Method B as described for Example 2.1 step 5. The only difference in the above reaction scheme was the use of 8-methyl-quinolin-5-ylamine instead of compound 4 as the reaction partner reaction step 3.

7-((1R,2S)-2-Amino-cyclohexylamino)-5-(8-methyl-quinolin-5-ylamino)-3H-pyrido[3,4-d]pyridazin-4-one

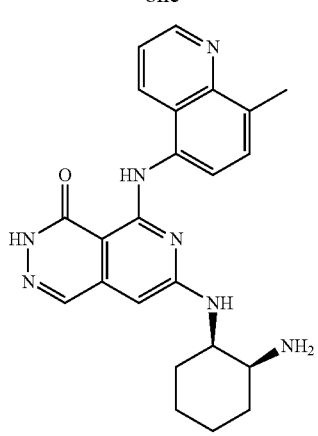

The compound was characterised after purification by preparative HPLC.

$^1$H-NMR (400 MHz; DMSO-d6, 25° C.): 12.40 (s, 1H); 12.00 (s, 1H); 9.00 (dd, 1H); 8.56 (d, 1H); 8.36 (br.s, 1H); 8.06 (s, 1H); 7.84-7.56 (m, 4H); 7.32 (br.s, 1H); 6.16 (s, 1H); 4.07 (br.s, 1H); 3.50 (br.s, 1H); 2.72 (s, 3H); 1.84-1.55 (m, 8H); UPLC/MS found for C23H25N7O as (M+H)$^+$416.1; UPLC retention time 0.60 min.

Example 2.14 was prepared following procedures similar to those described for Example 2.1. The BOC-deprotection was done by Method B as described for Example 2.1 step 5. The only difference in the above reaction scheme was the use of 7-amino-1H-indole-3-carbonitrile instead of compound 4 as the reaction partner reaction step 3.

7-[7-((1R,2S)-2-Amino-cyclohexylamino)-4-oxo-3,4-dihydro-pyrido[3,4-d]pyridazin-5-ylamino]-1H-indole-3-carbonitrile

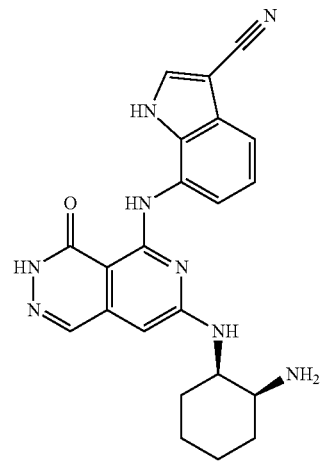 [SMILES: N#Cc1c[nH]c2c(Nc3nc(N[C@@H]4CCCC[C@@H]4N)cc4cn[nH]c(=O)c34)cccc12]

The compound was characterised after purification by preparative HPLC.

$^1$H-NMR (400 MHz; DMSO-d6, 25° C.): 12.28 (s, 1H); 11.96 (br.s, 1H); 10.96 (s, 1H); 8.20 (s, 1H); 8.01 (s, 1H); 7.56 (br.s, 2H); 7.49 (d, 1H); 7.40 (d, 1H); 7.24 (dd, 1H); 7.16 (br.s, 1H); 6.09 (s, 1H); 3.61 (br.s, 1H); 3.14 (br.s, 1H); 1.58-1.17 (m, 8H); UPLC/MS found for C22H22N8O as (M+H)$^+$ 415.0; UPLC retention time 0.64 min.

Example 2.15 was prepared following procedures similar to those described for Example 2.1. The BOC-deprotection was done by Method A as described for Example 2.1 step 5. The only difference in the above reaction scheme was the use of 7-methyl-1H-indol-4-ylamine instead of compound 4 as the reaction partner reaction step 3.

7-((1R,2S)-2-Amino-cyclohexylamino)-5-(7-methyl-1H-indol-4-ylamino)-3H-pyrido[3,4-d]pyridazin-4-one

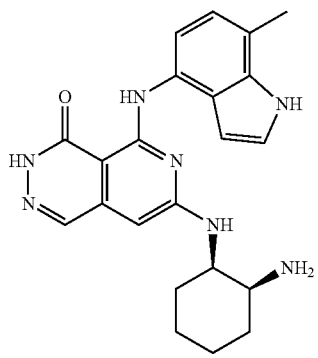 [SMILES: Cc1ccc(Nc2nc(N[C@@H]3CCCC[C@@H]3N)cc3cn[nH]c(=O)c23)c2cc[nH]c12]

The compound was characterised after purification by preparative HPLC.

$^1$H-NMR (400 MHz; DMSO-d6, 25° C.): 12.19 (br.s, 1H); 11.81 (s, 1H); 11.19 (s, 1H); 8.15-8.19 (d, 1H); 7.92 (s, 1H); 7.34-7.37 (t, 1H); 7.12-7.23 (br.s, 1H); 6.83-6.86 (d, 1H); 6.59-6.62 (m, 1H); 6.01 (s, 1H); 3.98-4.13 (m, 1H); 3.21-3.27 (m, 1H); 2.46 (s, 3H); 1.17-1.78 (m, 8H); UPLC/MS found for C22H25N7O as (M+H)$^+$ 404.1; UPLC retention time 0.68 min.

Example 2.16 was prepared following procedures similar to those described for Example 2.1. The BOC-deprotection was done by Method B as described for Example 2.1 step 5. The only difference in the above reaction scheme was the use of quinolin-5-ylamine instead of compound 4 as the reaction partner reaction step 3.

7-((1R,2S)-2-Amino-cyclohexylamino)-5-(quinolin-5-ylamino)-3H-pyrido[3,4-d]pyridazin-4-one

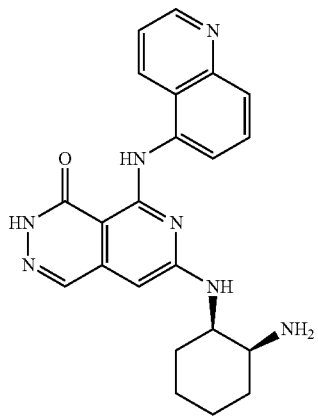 [SMILES: N[C@H]1CCCC[C@H]1Nc1cc2cn[nH]c(=O)c2c(Nc2cccc3ncccc23)n1]

The compound was characterised after purification by preparative HPLC.

$^1$H-NMR (400 MHz; DMSO-d6, 25° C.): 12.45 (s, 1H); 12.21 (s, 1H); 9.08-8.89 (dd, 1H); 8.65 (d, 1H); 8.58 (br.s, 1H); 8.09 (s, 1H); 7.92-7.76 (m, 5H); 7.37 (br.s, 1H); 6.21 (s, 1H); 4.15 (br.s, 1H); 3.53 (br.s, 1H); 1.84-1.35 (m, 8H); UPLC/MS found for C22H23N7O as (M+H)$^+$ 402.3; UPLC retention time 0.62 min.

Example 2.17 was prepared following procedures similar to those described for Example 2.1. The BOC-deprotection was done by Method A as described for Example 2.1 step 5. The only difference in the above reaction scheme was the use of 2-methyl-1H-indol-4-ylamine instead of compound 4 as the reaction partner reaction step 3.

7-((1R,2S)-2-Amino-cyclohexylamino)-5-(2-methyl-1H-indol-4-ylamino)-3H-pyrido[3,4-d]pyridazin-4-one

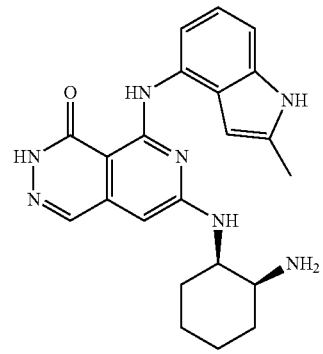 [SMILES: Cc1cc2c(Nc3nc(N[C@@H]4CCCC[C@@H]4N)cc4cn[nH]c(=O)c34)cccc2[nH]1]

The compound was characterised after purification by preparative HPLC.

$^1$H-NMR (400 MHz; DMSO-d6, 25° C.): 12.15 (br.s, 1H); 11.75 (s, 1H); 10.99 (s, 1H) 8.17-8.26 (s, 1H); 7.09-7.22 (m, 1H); 6.94-7.00 (m, 2H); 6.29-6.32 (m, 1H); 6.05 (s, 1H); 3.97-4.13 (m, 1H); 3.19-3.24 (m, 1H); 2.45 (s, 3H); 1.22-1.79 (m, 8H); UPLC/MS found for C22H25N7O as (M+H)$^+$ 404.1; UPLC retention time 0.67 min.

Example 2.18 was prepared following procedures similar to those described for Example 2.1. The BOC-deprotection was done by Method B as described for Example 2.1 step 5. The only difference in the above reaction scheme was the use of quinoxalin-6-ylamine instead of compound 4 as the reaction partner reaction step 3.

7-((1R,2S)-2-Amino-cyclohexylamino)-5-(quinoxalin-6-ylamino)-3H-pyrido[3,4-d]pyridazin-4-one

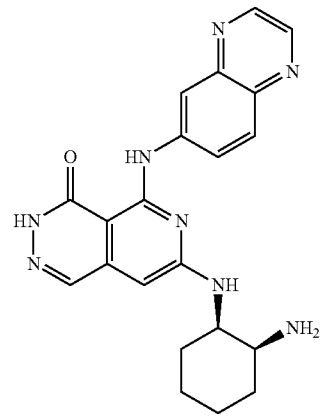 [SMILES: N[C@H]1CCCC[C@H]1Nc1cc2cn[nH]c(=O)c2c(Nc2ccc3nccnc3c2)n1]

The compound was characterised after purification by preparative HPLC.

$^1$H-NMR (400 MHz; DMSO-d6, 25° C.): 12.35 (br.s, 1H); 8.95 (d, 2H); 8.80 (s, 1H); 8.04 (br.s, 2H); 7.85 (s, 1H); 6.20 (s, 1H); 4.24 (br.s, 1H); 3.44 (br.s, 1H); 1.95-1.20 (m, 8H); UPLC/MS found for C21H22N8O as (M+H)$^+$ 403.1; UPLC retention time 0.62 min.

Example 2.19 was prepared following procedures similar to those described for Example 2.1. The BOC-deprotection was done by Method B as described for Example 2.1 step 5. The only difference in the above reaction scheme was the use of quinolin-7-ylamine instead of compound 4 as the reaction partner reaction step 3.

7-((1R,2S)-2-Amino-cyclohexylamino)-5-(quinolin-7-ylamino)-3H-pyrido[3,4-d]pyridazin-4-one

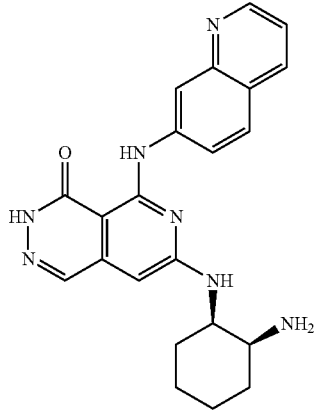 [SMILES: N[C@H]1CCCC[C@H]1Nc1cc2cn[nH]c(=O)c2c(Nc2ccc3cccnc3c2)n1]

The compound was characterised after purification by preparative HPLC.

¹H-NMR (400 MHz; DMSO-d6, 25° C.): 12.25 (br.s, 1H); 11.88 (s, 1H); 8.83 (dd, 1H); 8.76 (d, 1H); 8.28 (d, 1H); 7.96 (s, 1H); 7.94 (s, 1H); 7.72 (dd, 1H); 7.36 (dd, 1H); 7.30-7.22 (m, 1H); 6.16 (s, 1H); 4.18 (br.s, 1H); 3.20 (br.s, 1H); 1.85-1.20 (m, 8H); UPLC/MS found for C22H23N7O as (M+H)⁺ 402.1; UPLC retention time 0.54 min.

Example 2.20 was prepared following procedures similar to those described for Example 2.1. The BOC-deprotection was done by Method B as described for Example 2.1 in step 5. The only difference in the above reaction scheme was the use of quinolin-8-ylamine instead of compound 4 as the reaction partner reaction step 3.

7-((1R,2S)-2-Amino-cyclohexylamino)-5-(quinolin-8-ylamino)-3H-pyrido[3,4-d]pyridazin-4-one

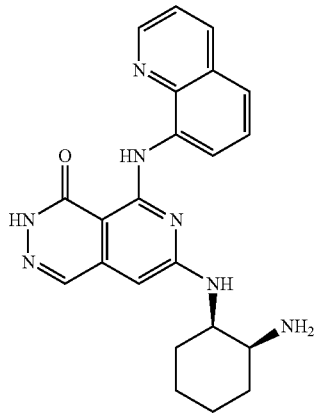 [SMILES: N[C@H]1CCCC[C@H]1Nc1cc2cn[nH]c(=O)c2c(Nc2cccc3cccnc23)n1]

The compound was characterised after purification by preparative HPLC.

¹H-NMR (400 MHz; DMSO-d6, 25° C.): 13.03 (s, 1H); 12.21 (s, 1H); 9.05 (br.s, 1H); 8.95 (dd, 1H); 8.39 (dd, 1H); 8.02 (s, 1H); 7.84 (br.s, 2H); 7.68-7.51 (m, 3H); 7.35 (br.s, 1H); 6.21 (s, 1H); 4.40 (br.s, 1H); 3.74 (br.s, 1H); 1.93-1.42 (m, 8H); UPLC/MS found for C22H23N7O as (M+H)⁺ 402.3; UPLC retention time 0.74 min.

Example 3.1

7-((3R,4R)-3-Amino-tetrahydro-pyran-4-ylamino)-5-(3-methyl-1H-indol-7-ylamino)-3H-pyrido[3,4-d]pyridazin-4-one Example 3.1 was synthesized in accordance to Scheme 3 shown below.

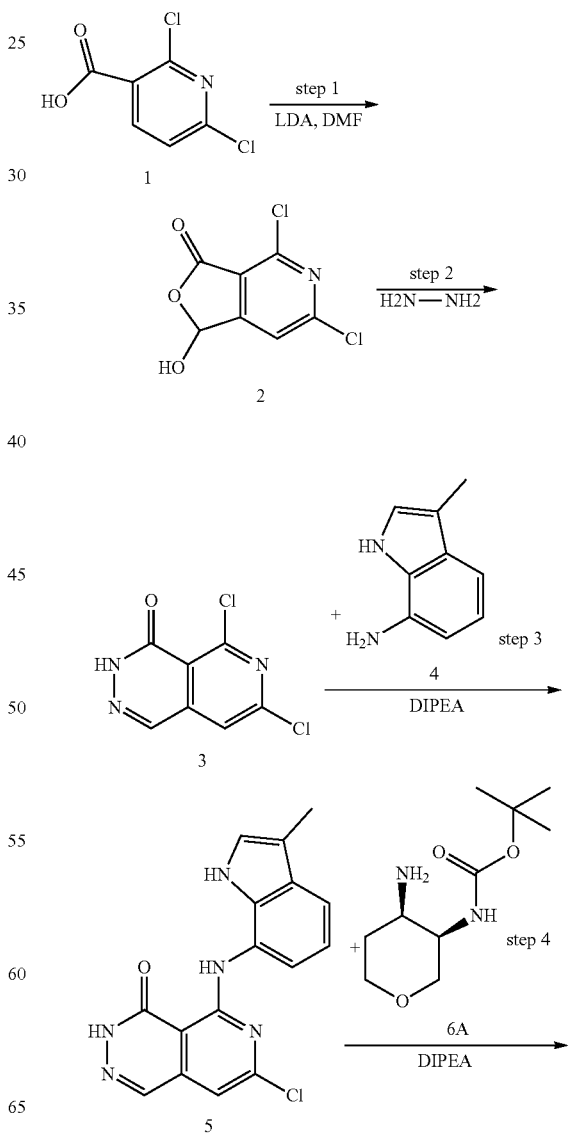

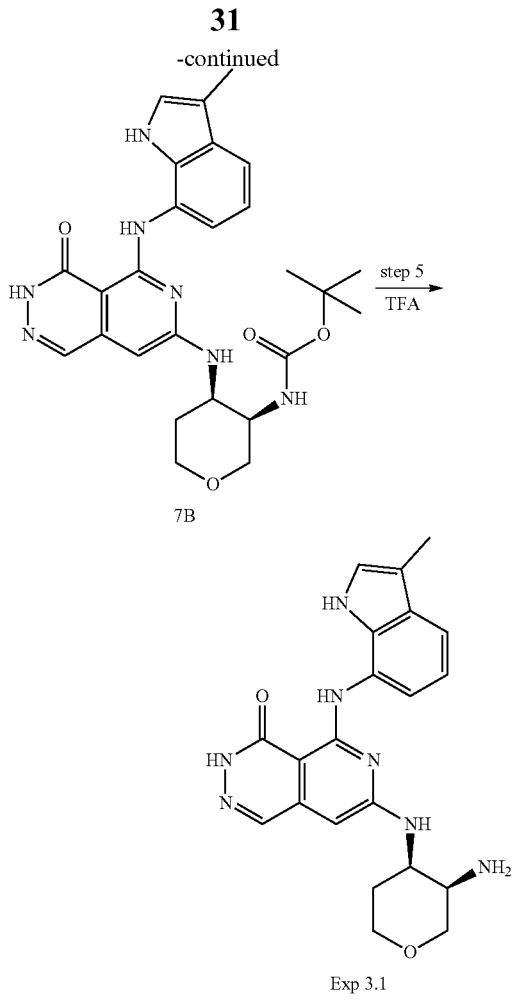

Step 1-Step 3 as described for Example 2.1

Step 4: {(3R,4R)-4-[5-(3-Methyl-1H-indol-7-ylamino)-4-oxo-3,4-dihydro-pyrido[3,4 d]-pyridazin-7-ylamino]-tetrahydro-pyran-3-yl}-carbamic acid tert-butyl ester To a solution of 5,7-dichloro-3H-pyrido[3,4-d]pyridazin-4-one (100 mg) in NMP (1 ml) in a microwave tube DIPEA (0.107 ml) and ((3R,4R)-4-amino-tetrahydro-pyran-3-yl)-carbamic acid tert-butyl ester (133 mg) was added. The tube was capped and heated on a sandbath at 100° C. for 3 days. After cooling to room temperature the reaction mixture was diluted with 30 ml of EtOAc and washed with brine (2×50 ml). Aqueaous phases were re-extracted with EtOAc (30 ml) and combined organic phases were dried and evaporated to dryness leaving a yellow solid. Purification was effected via flash chromatography.

Step 5: 7-((3R,4R)-3-aminotetrahydro-2H-pyran-4-ylamino)-5-(3-methyl-1H-indol-7-ylamino)pyrido[4,3-d]pyridazin-4(3H)-one To a solution of {(3R,4R)-4-[5-(3-Methyl-1H-indol-7-ylamino)-4-oxo-3,4-dihydro-pyrido[3,4-d]pyridazin-7-ylamino]-tetrahydro-pyran-3-yl}-carbamic acid tert-butyl ester (76 mg) in DCM was added TFA (0.347 ml). The reaction mixture was stirred for 1 h at RT, diluted with EtOAc (30 ml) and washed with 5% Na$_2$CO$_3$ solution (20 ml) and water (2×30 ml). The aqueous phases were re-extracted with EtOAc (30 ml) and the combined organic layers were dried and evaporated to yield a yellow solid. The crude product was purified by preparative HPLC to yield the product as a yellow solid.

$^1$H-NMR (400 MHz, DMSO-d$_6$): 12.12 (br.s, 1H); 10.96 (s, 1H); 10.35 (s, 1H); 7.91 (s, 1H); 7.23-7.43 (m, 2H); 6.88-7.11 (m, 3H); 6.00 (s, 1H); 3.62-3.86 (m, 2H); 3.51 (d, 1H); 3.18 (d, 1H); 3.10 (br.s, 1H); 2.62-2.76 (m, 1H); 2.28 (d, 3H); 1.54-1.70 (m, 1H); 1.49 (br.s, 1H); 1.41 (d, 1H); UPLC/MS found for C21H23N7O2 as (M+H)$^+$ 406.2; UPLC retention time 0.67 min.

Example 3.2 was prepared following procedures similar to those described for Example 3.1. The only difference in the above reaction scheme was the use of benzo[b]thiophen-4-ylamine instead of compound 4 as the reaction partner reaction step 3.

7-((3R,4R)-3-Amino-tetrahydro-pyran-4-ylamino)-5-(benzo[b]thiophen-4-ylamino)-3H-pyrido[3,4-d]pyridazin-4-one The compound was characterised after purification by preparative HPLC.

$^1$H-NMR (400 MHz; DMSO-d6, 25° C.): 12.43 (s, 1H); 12.08 (s, 1H); 8.37 (br.s, 1H); 8.08 (s, 1H); 7.94 (br.s, 2H); 7.86 (d, 1H); 7.73 (d, 1H); 7.60 (d, 1H); 7.56 (br.s, 1H); 7.43 (t, 1H); 6.15 (s, 1H); 4.26 (br.s, 1H); 3.99 (dd, 1H); 3.91 (d, 1H); 3.70 (br.s, 1H); 3.68-3.57 (m, 2H); 2.03 (qd, 1H); 1.76 (d, 1H); UPLC/MS found for C20H20N6O2S as (M+H)$^+$ 409.3; UPLC retention time 0.69 min.

Example 3.3 was prepared following procedures similar to those described for Example 3.1. The only difference in the above reaction scheme was the use of 5-fluoro-3-methyl-1H-indol-7-ylamine as the reaction partner reaction step 3.

7-((3R,4R)-3-Amino-tetrahydro-pyran-4-ylamino)-5-(5-fluoro-3-methyl-1H-indol-7-ylamino)-3H-pyrido[3,4-d]pyridazin-4-one The compound was characterised after purification by preparative HPLC.

$^1$H-NMR (400 MHz; DMSO-d6, 25° C.): 12.34 (s, 1H); 11.08 (s, 1H); 10.58 (s, 1H); 8.04 (s, 1H); 7.82 (br.s, 3H); 7.38 (br.s, 2H); 7.15 (s, 1H); 7.08 (dd, 1H); 6.09 (s, 1H); 3.83-3.98 (m, 2H); 3.69 (d, 1H); 3.62-3.22 (m, 3H); 2.28 (s, 3H); 1.91 (dd, 1H); 1.62 (d, 1H); UPLC/MS found for C21H22FN7O2 as (M+H)$^+$ 424.2; UPLC retention time 0.72 min.

Example 3.4 was prepared following procedures similar to those described for Example 3.1. The BOC-deprotection was done by Method A as described for Example 2.1 step 5. The only difference in the above reaction scheme was the use of 1H-indol-7-ylamine instead of compound 4 as the reaction partner reaction step 3.

7-((3R,4R)-3-Amino-tetrahydro-pyran-4-ylamino)-5-(1H-indol-7-ylamino)-3H-pyrido[3,4-d]pyridazin-4-one

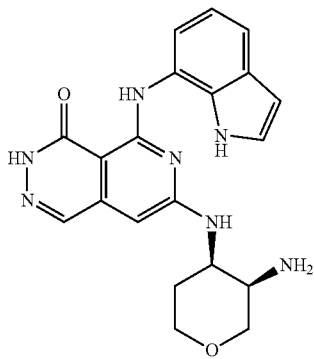 [SMILES: N[C@H]1COCC[C@H]1Nc1cc2cn[nH]c(=O)c2c(Nc2cccc3cc[nH]c23)n1]

The compound was characterised after purification by preparative HPLC.

$^1$H-NMR (400 MHz; DMSO-d6, 25° C.): 12.15 (br.s, 1H); 11.00 (s, 1H); 10.75 (s, 1H); 7.92 (s, 1H); 7.35-7.39 (d, 1H); 7.29-7.34 (d, 1H); 7.25-7.28 (t, 1H); 7.00-7.14 (br.s., 1H); 6.95-7.00 (t, 1H); 6.45-6.48 (m, 1H), 6.01 (s, 1H); 3.52-3.75 (m, 2H); 3.45-3.54 (m, 1H); 3.10-3.19 (m, 2H); 1.35-1.69 (m, 2H); UPLC/MS found for C21H23N7O as (M+H)$^+$ 392.1; UPLC retention time 0.58 min.

Biopharmaceutical Part

The compounds of the invention in free form or in pharmaceutically acceptable salt form, exhibit valuable pharmacological properties as described in the tests below, and are therefore indicated for therapy.

SYK Enzyme Assay

A number of compounds of the present invention were assayed in a chip based microfluidic mobility shift assay. All assays were performed in 384 well microtiter plates. Each assay plate contained 8-point serial dilutions for 40 test compounds, as well as four 8-point serial dilutions of staurosporine as reference compound, plus 16 high- and 16 low controls. Liquid handling and incubation steps were done on a Thermo CatX workstation equipped with a Innovadyne Nanodrop Express. Between pipetting steps, tips were cleaned in wash cycles using wash buffer. The assay plates were prepared by addition of 50 nl per well of compound solution in 90% DMSO. The kinase reactions were started by stepwise addition of 4.5 μl per well of peptide/ATP-solution (50 mM HEPES, pH 7.5, 1 mM DTT, 0.02% Tween20, 0.02% BSA, 0.6% DMSO, 10 mM beta-glycerophosphate, and 10 μM sodium orthovanadate, 1 mM MgCl$_2$, 3 mM MnCl$_2$, 4 μM ATP, 4 μM peptide (5-Fluo-Ahx-GAPDYENLQELNKK-Amid) and 4.5 μl per well of enzyme solution (50 mM HEPES, pH 7.5, 1 mM DTT, 0.02% Tween20, 0.02% BSA, 0.6% DMSO, 10 mM beta-glycerophosphate, and 10 μM sodium orthovanadate, 1 mM MgCl$_2$, 3 mM MnCl$_2$, 4 nM SYK (SYK(2-635), produced in-house from insect cells). Kinase reactions were incubated at 30° C. for 60 minutes and subsequently terminated by addition of 16 μl per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of "pre-dilution plates", "master plates" and "assay plates".

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 30 μL of individual compound dilutions including standard compound and controls of the 4 "pre-dilution plates" were transferred into a 384 "master plate" including the following concentrations 1'810, 362, 72.5, 54.6, 14.5, 2.9, 0.58 and 0.12 μM, respectively in 90% of DMSO.

Assay plates: Identical "assay plates" were then prepared by pipetting 50 nL each of compound dilutions of the "master plates" into 384-well "assay plates" by means of a Humming-Bird 384-channel dispenser. These plates were used directly for the assay which was performed in a total volume of 9.05 μL. This led to a final compound concentration of 10, 2.0, 0.4, 0.08, 0.016, 0.0032, 0.00064 and 0.000128 μM and a final DMSO concentration of 0.5% in the assay.

In this assay, the compounds of the invention had IC$_{50}$ values provided infra:

| Example | IC50 [μM] |
|---------|-----------|
| 1.1 | 0.002 |
| 1.2 | 0.044 |
| 2.1 | 0.0016 |
| 2.2 | 0.0006 |

-continued

| Example | IC50 [µM] |
|---|---|
| 2.3 | 0.0011 |
| 2.4 | 0.0013 |
| 2.5 | 0.0016 |
| 2.6 | 0.002 |
| 2.7 | 0.0021 |
| 2.8 | 0.0023 |
| 2.9 | 0.0027 |
| 2.10 | 0.0052 |
| 2.11 | 0.0054 |
| 2.12 | 0.007 |
| 2.13 | 0.007 |
| 2.14 | 0.008 |
| 2.15 | 0.009 |
| 2.16 | 0.009 |
| 2.17 | 0.016 |
| 2.18 | 0.026 |
| 2.19 | 0.042 |
| 2.20 | 0.045 |
| 3.1 | 0.009 |
| 3.2 | 0.0018 |
| 3.3 | 0.002 |
| 3.4 | 0.032 |

[uM] or [µM] means micromol

Utility Section

The compounds of the invention are therefore generally useful in the prevention or treatment of disorders or diseases where for example SYK inhibition plays a role, e.g. diseases or disorders mediated by B lymphocytes, myeloid cells, neutrophils, mast cells, platelets and/or eosinophils e.g. acute or chronic rejection of organ or tissue allo- or xenografts, atheriosclerosis, vascular occlusion due to vacular injury such as angioplasty, restenosis, hypertension, heart failure, chronic obstructive pulmonary disease, CNS disease such as Alzheimer disease or amyotrophic lateral sclerosis, cancer, infectious disease such as AIDS, septic shock or adult respiratory distress syndrome, ischemia/reperfusion injury e.g. myocardial infarction, stroke, gut ischemia, renal failure or hemorrhage shock, or traumatic shock.

The agent of the invention are also useful in the treatment and/or prevention of acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes (type I and II) and the disorders associated therewith, vascular manifestations of autoimmune and inflammatory diseases (vasculitides), respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis. Immune and/or idiopathic thrombocytopenia, allergies, wound healing, graft vs host disease, Compounds of the invention are also useful in the prevention or treatment of tumors, for example brain and other central nervous system tumors (e.g. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites, tumors of blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type e.g. diffuse large B cell lymphomas, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia.

Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is.

Dosage(s), Administration(s):

For the above uses the required dosage will of course vary depending on the mode of administration, the particular condition to be treated and the effect desired. In general, satisfactory results are indicated to be obtained systemically at daily dosages of from about 0.02 to 25 mg/kg per body weight. An indicated daily dosage in the larger mammal, e.g. humans, may be typically in the range from about 0.2 mg to about 2 g, conveniently administered, for example, in divided doses up to four times a day or in retard form. Suitable unit dosage forms for oral administration may typically comprise from ca. 0.1 to 500 mg active ingredient.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration may for example be to the skin. A further form of topical administration may be to the eye. Pharmaceutical compositions comprising a compound of the invention in association with at least one pharmaceutical acceptable carrier or diluent may be manufactured in conventional manner by mixing with a pharmaceutically acceptable carrier or diluent.

The compounds of the invention may be administered in free form or in pharmaceutically acceptable salt form, e.g. as indicated above. Such salts may be prepared in conventional manner and may typically exhibit the same order of activity as the free compounds.

Combinations:

Compounds of the invention may be administered as the sole active ingredient or together with other drugs useful against neoplastic diseases, inflammatory disorders or in immunomodulating regimens. For example, the compounds of the invention may be used in combination with an active agent effective in various diseases as described above, e.g. with cyclosporins, rapamycins or ascomycins, or their immunosuppressive analogs or derivatives, e.g. cyclosporin A, cyclosporin G, Isa tx247, FK-506, sirolimus or everolimus; corticosteroids e.g. prednisone; cyclophosphamide; azathioprine; methotrexate; gold salts, sulfasalazine, antimalarials; leflunomide; mizoribine; mycophenolic acid; mycophenolate mofetil; 15-deoxyspergualine; an EDG receptor agonist having accelerating lymphocyte homing activity, e.g. FTY720 or an analogue thereof, immuno-suppressive monoclonal antibodies, e.g. monoclonal antibodies to leukocyte receptors, e.g. MHC, CD2, CD3, CD4, CD7, CD25, CD28, CD40, CD45, CD58, CD80, CD86, CD152, CD137, CD154, ICOS, LFA-1, VLA-4 or their ligands; or other immunomodulatory compounds, e.g. CTLA4Ig.

A compound of the invention may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. A combination of the invention comprising an antineoplastic agent which is an aromatase inhibitor may particularly be useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride.

The term "topoisomerase I inhibitors" as used herein includes, but is not limited to topotecan, irinotecan, 9-nitro-camptothecin and the macromolecular camptothecin conjugate PNU-166148 (compound A1 in WO99/17804).

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D.

The term "alkylating agents" as used herein includes, but is not limited to cyclophosphamide, ifosfamide and melphalan.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs), and anti-angiogenic compounds having another mechanism of action than decreasing the protein kinase activity.

The term "gonadorelin agonist" as used herein includes, but is not limited to abarelix, goserelin and goserelin acetate. Goserelin is disclosed in U.S. Pat. No. 4,100,274.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having aniproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

In accordance with the foregoing, the present invention provides:

(1) A compound of formula (I) or formula (II) or a pharmaceutically acceptable salt thereof, especially for use as a pharmaceutical.

(2) A compound of formula (I) or formula (II) or a pharmaceutically acceptable salt thereof, for use as a SYK inhibitor, for example for use in any of the particular indications hereinbefore set forth.

(3) A pharmaceutical composition, e.g. for use in any of the indications herein before set forth, comprising a compound of formula (I) or formula (II) or a pharmaceutically acceptable salt thereof, together with one or more pharmaceutically acceptable diluents or carriers therefor.

(4) A method for the treatment of any of particular indication hereinbefore set forth in a subject in need thereof which comprises administering an effective amount of a compound of formula (I) or formula (II) or a pharmaceutically acceptable salt thereof;

(5) The use of a compound of formula (I) or formula (II) or a pharmaceutically acceptable salt thereof, in the manufacture of a medicament for the treatment or prevention of a disease or condition in which SYK tyrosine kinase activation plays a role or is implicated; e.g. as discussed above.

(6) A combination comprising a compound of formula (I) or formula (II) or a pharmaceutically acceptable salt thereof, and at least a second drug substance wherein said second drug substance may be selected from anti-neoplastic agents, anti-inflammatory agents, immunomodulating agents and antiproliferative agents as set forth hereinbefore.

The invention claimed is:

1. A compound of the formula (I) or a pharmaceutically acceptable salt thereof,

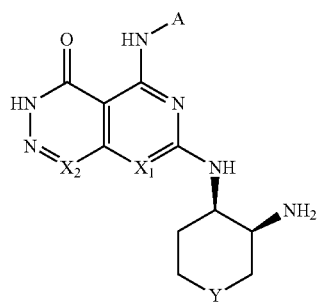

(I)

wherein
X1 is CR1;
X2 is CH;
Y is $CH_2$ or O;
A is bicyclic hetereoaryl having from 8 to 10 ring atoms, wherein 1-3 of said ring atoms are heteroatoms selected from N, O and S and wherein said heteroaryl may be unsubstituted of substituted at a carbon atom by a R2 or at a nitrogen atom by a R3;
R1 is H, Hal or $C_{1-4}$ alkyl;
R2 is H, $C_{1-4}$ alkyl, $C_{3-5}$ cycloalkyl, CN or Hal; and
R3 is H or alkyl.

2. A compound of claim 1, or a pharmaceutically acceptable salt thereof, wherein
X1 is CH;
X2 is CH;
Y is $CH_2$;
A is bicyclic hetereoaryl having from 8 to 10 ring atoms, wherein 1-2 of said ring atoms are heteroatoms selected from N, O and S and wherein said heteroaryl may be unsubstituted of substituted at a carbon atom by a R2 and at a nitrogen atom by a R3;
R2 is H, $C_{1-4}$ alkyl, $C_{3-5}$ cycloalkyl, CN or Hal; and
R3 is H or alkyl.

3. A compound of claim 1, or a pharmaceutically acceptable salt thereof, wherein
X1 is CH;
X2 is CH;
Y is $CH_2$;
A is an unsubstituted or substituted indole moiety, wherein the substituent is R2 and is attached to a carbon atom of the indole moiety; wherein
R2 is $C_{1-4}$ alkyl.

4. A compound of claim 1, which is a compound of formula (II) or a pharmaceutically acceptable salt thereof, wherein

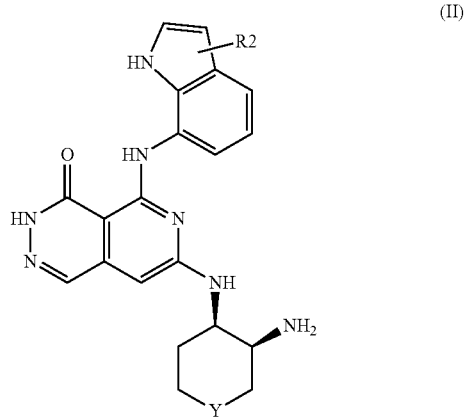

(II)

Y is $CH_2$ or 0; and
R2 is H, $C_{1-4}$alkyl or Hal.

5. A compound of claim 4, or a pharmaceutically acceptable salt thereof, wherein
Y is $CH_2$; and
R2 is H, or $C_{1-4}$alkyl or Hal.

6. A compound of claim 1, or a pharmaceutically acceptable salt thereof, which is selected from:
7-((1R,2S)-2-Amino-cyclohexylamino)-8-fluoro-5-(5-fluoro-3-methyl-1H-indol-7-ylamino)-3H-pyrido[3,4-d]pyridazin-4-one,
7-((1R,2S)-2-Amino-cyclohexylamino)-8-fluoro-5-(quinolin-5-ylamino)-3H-pyrido[3,4-d]pyridazin-4-one,
7-((1R,2S)-2-Amino-cyclohexylamino)-5-(3-methyl-1H-indol-7-ylamino)-3H-pyrido[3,4-d]pyridazin-4-one,
7-((1R,2S)-2-Amino-cyclohexylamino)-5-(1-methyl-1H-indol-4-ylamino)-3H-pyrido[3,4-d]pyridazin-4-one,
7-((1R,2S)-2-Amino-cyclohexylamino)-5-(2-methyl-2H-indazol-4-ylamino)-3H-pyrido[3,4-d]pyridazin-4-one,
7-((1R,2S)-2-Amino-cyclohexylamino)-5-(5-fluoro-3-methyl-1H-indol-7-ylamino)-3H-pyrido[3,4-d]pyridazin-4-one,
7-((1R,2S)-2-Amino-cyclohexylamino)-5-(quinolin-6-ylamino)-3H-pyrido[3,4-d]pyridazin-4-one,
7-((1R,2S)-2-Amino-cyclohexylamino)-5-(benzofuran-4-ylamino)-3H-pyrido[3,4-d]pyridazin-4-one,
7-((1R,2S)-2-Amino-cyclohexylamino)-5-(benzo[b]thiophen-4-ylamino)-3H-pyrido[3,4-d]pyridazin-4-one,
7-((1R,2S)-2-Amino-cyclohexylamino)-5-(2-methyl-quinolin-5-ylamino)-3H-pyrido[3,4-d]pyridazin-4-one,
7-((1R,2S)-2-Amino-cyclohexylamino)-5-(1H-indol-4-ylamino)-3H-pyrido[3,4-d]pyridazin-4-one, 7-((1R,2S)-2-Amino-cyclohexylamino)-5-(1H-indazol-4-ylamino)-3H-pyrido[3,4-d]pyridazin-4-one, 7-((1R,2S)-2-Amino-cyclohexylamino)-5-(quinolin-3-ylamino)-3H-pyrido[3,4-d]pyridazin-4-one, 7-((1R,2S)-2-Amino-cyclohexylamino)-5-(1H-indol-7-ylamino)-3H-pyrido[3,4-d]pyridazin-4-one, 7-((1R,2S)-2-Amino-cyclohexylamino)-5-(8-methyl-quinolin-5-ylamino)-3H-pyrido[3,4-d]pyridazin-4-one, 7-[7-((1R,2S)-2-Amino-cyclohexylamino)-4-oxo-3,4-dihydro-pyrido[3,4-d]pyridazin-5-ylamino]-1H-indole-3-carbonitrile, 7-((1R,2S)-2-Amino-cyclohexylamino)-5-(7-methyl-1H-indol-4-ylamino)-3H-pyrido[3,4-d]pyridazin-4-one, 7-((1R,2S)-2-Amino-cyclohexylamino)-5-(quinolin-5-ylamino)-3H-pyrido[3,4-d]pyridazin-4-one, 7-((1R,2S)-2-Amino-cyclohexylamino)-5-(2-methyl-1H-indol-4-ylamino)-3H-pyrido[3,4-d]pyridazin-4-one, 7-((1R,2S)-2-Amino-cyclohexylamino)-5-(quinoxalin-6-ylamino)-3H-pyrido[3,4-d]pyridazin-4-one, 7-((1R,2S)-2-Amino-cyclohexylamino)-5-(quinolin-7-ylamino)-3H-pyrido[3,4-d]pyridazin-4-one, 7-((1R,2S)-2-Amino-cyclohexylamino)-5-(quinolin-8-ylamino)-3H-pyrido[3,4-d]pyridazin-4-one, 7-((3R,4R)-3-Amino-tetrahydro-pyran-4-ylamino)-5-(3-methyl-1H-indol-7-ylamino)-3H-pyrido[3,4-d]pyridazin-4-one, 7-((3R,4R)-3-Amino-tetrahydro-pyran-4-ylamino)-5-(benzo[b]thiophen-4-ylamino)-3H-pyrido[3,4-d]pyridazin-4-one, 7-((3R,4R)-3-Amino-tetrahydro-pyran-4-ylamino)-5-(5-fluoro-3-methyl-1H-indol-7-ylamino)-3H-pyrido[3,4-d]pyridazin-4-one, and 7-((3R,4R)-3-Amino-tetrahydro-pyran-4-ylamino)-5-(1H-indol-7-ylamino)-3H-pyrido[3,4-d]pyridazin-4-one.

7. A pharmaceutical composition comprising a therapeutically effective amount of a compound according to claim 1 or a pharmaceutically acceptable salt thereof and one or more pharmaceutically acceptable carriers.

8. A combination comprising a therapeutically effective amount of a compound according to claim 1 or a pharmaceutically acceptable salt thereof and one or more therapeutically active co-agents.

9. A method of modulating SYK activity in a subject, wherein the method comprises administering to the subject a therapeutically effective amount of the compound according to claim 1.

* * * * *